(12) United States Patent
Dumas

(10) Patent No.: US 7,722,354 B1
(45) Date of Patent: May 25, 2010

(54) ORTHODONTIC CONNECTOR ASSEMBLY AND A METHOD FOR TREATING TEETH

(76) Inventor: John Joseph Dumas, 3460 Broomcrest Dr., Bloomfield Hills, MI (US) 48304-2517

(*) Notice: Subject to any disclaimer, the term of this patent is extended or adjusted under 35 U.S.C. 154(b) by 58 days.

(21) Appl. No.: 11/540,293

(22) Filed: Sep. 29, 2006

(51) Int. Cl.
*A61C 3/00* (2006.01)

(52) U.S. Cl. .......................................................... 433/8

(58) Field of Classification Search .............. 433/8–17, 433/24
See application file for complete search history.

(56) References Cited

U.S. PATENT DOCUMENTS

| | | | | |
|---|---|---|---|---|
| 3,959,880 | A | * | 6/1976 | Andrews ...................... 433/11 |
| 3,975,824 | A | * | 8/1976 | Lee ............................. 433/14 |
| 4,180,912 | A | * | 1/1980 | Kesling ....................... 327/437 |
| 4,427,381 | A | * | 1/1984 | Hall ............................. 433/14 |
| 4,496,318 | A | * | 1/1985 | Connelly, Jr. ................. 433/14 |
| 4,525,143 | A | | 6/1985 | Adams |
| 4,585,413 | A | * | 4/1986 | Wool ............................. 433/8 |
| 4,957,438 | A | | 9/1990 | Bax |
| 5,580,243 | A | | 12/1996 | Bloore |
| 6,726,474 | B2 | | 4/2004 | Spencer |
| 2002/0058227 | A1 | | 5/2002 | Townsend-Hansen |
| 2004/0157184 | A1 | | 8/2004 | Reising |
| 2005/0255422 | A1 | | 11/2005 | Cordato |
| 2005/0277082 | A1 | | 12/2005 | Christoff |
| 2006/0199137 | A1 | | 9/2006 | Abels et al. |
| 2006/0269891 | A1 | * | 11/2006 | Miqui ......................... 433/16 |

* cited by examiner

*Primary Examiner*—Cris L Rodriguez
*Assistant Examiner*—Sunil K Singh
(74) *Attorney, Agent, or Firm*—John G. Chupa

(57) ABSTRACT

An orthodontic connector assembly (10) including a plurality of substantially identical connecting members, such as members (12), (14) which include a movable but biased portion (20) which is adapted to selectively and removably receive a pocket portion (44) which is deployed on at least one bracket, such as bracket (40).

4 Claims, 2 Drawing Sheets

ORTHODONTIC CONNECTOR ASSEMBLY AND A METHOD FOR TREATING TEETH

FIELD OF THE INVENTION

The present invention generally relates to an orthodontic connector assembly and to a method for treating teeth and more particularly, to an assembly which allows orthodontic brackets, even a plurality of dissimilar brackets, to be selectively and removably coupled to teeth in a manner which forms a method for effectively treating teeth.

BACKGROUND OF THE INVENTION

Orthodontic brackets, often referred to as "braces" are devices which are normally and selectively affixed to the teeth of an individual, by the use of cement or another type of bonding agent, and are adapted to selectively receive a wire which is formed and deployed in the mouth of a patient in order to provide therapeutic force or pressure on the patient's teeth. The combination of the brackets and the wire are often sometimes collectively referred to as a "retaining system" or an "orthodontic retaining system".

While such prior and currently utilized retaining systems do allow therapeutic pressure to be applied to a patient's teeth, they suffer from some drawbacks.

By way of example and without limitation, as the therapy is applied to the patient (i.e., over time) modifications may need to be made to the brackets or different brackets may be optimally needed. This "bracket modification" or "replacement" is complicated and time consuming because the currently utilized brackets must be forcibly removed from the patient's teeth (e.g., removed from the cement or adhering agent), the teeth must be cleaned and "re-prepped" (an etching agent and a new application of an adhering agent must be deployed on the teeth), and the new or modified brackets must be deployed on the newly prepped teeth. The process is uncomfortable to the patient and is relatively costly due to the need for additional etching and adhesive material and the time needed to achieve the change or modification. Moreover, sometimes the deployed brackets become broken or are in need of repair and must be removed from the patient's teeth to become serviced, thereby requiring the same sort of afore-described process and cost and discomfort.

Further, it may be therapeutically desirable to deploy different sorts or types of brackets upon the teeth of a patient within a relatively short amount of time due to the needs of the patient and such "rapid bracket deployment" undesirably and greatly increases the cost and discomfort to the patient. Further, different sorts of brackets may be used on a patient, within a certain time, just in order for a orthodontist to evaluate the efficacy of these deployed brackets on certain patient and discover the bracket type which may provide optimal therapy on a patient (i.e., each patient may experience different amounts and types of therapy with a certain bracket). Non-limiting examples of orthodontic brackets are found within United States Patent Application Publication Numbers US2005/0255422 A1, US2002/0058227 A1, and US2004/0157184 A1 which are each fully and completely incorporated herein by reference, word for word and paragraph for paragraph.

There is therefore a need for a new and improved connector assembly which allows brackets to be easily, quickly, and cost effectively deployed upon the teeth of a patient and it is one non-limiting object of the present invention to provide such an improved connector system.

SUMMARY OF THE INVENTION

It is a first non-limiting object of the present invention to provide a new and novel orthodontic connector assembly which overcome some or all of the previously delineated disadvantages of prior connector systems.

It is a second non-limiting object of the present invention to provide a new and improved methodology for treating teeth which overcome some or all of the previously delineated disadvantages of prior and current strategies and methodologies.

According to a first non-limiting aspect of the present invention, an orthodontic connector assembly is provided and includes a plurality of substantially identical connector members which are each selectively and respectively adhered to unique teeth and each of which include a substantially identical connector portion, wherein each of the substantially identical connector portions cooperatively and removably receive a bracket assembly.

According to a second non-limiting aspect of the present invention, an orthodontic connector assembly is provided and includes the combination of a plurality of substantially identical connector members which each include a first smooth surface which is respectively and selectively adhered to unique teeth and each of which further respectively include a second opposed surface which includes a deformable connector and wherein each of the deformable connectors are substantially identical and have a certain first shape; and a plurality of brackets which include a first back surface having a plurality of substantially identical second connectors and wherein each of the substantially identical second connectors are adapted to receive a unique one of each of the first plurality of connectors and wherein each of the plurality of brackets include dissimilar front portions.

According to a third non-limiting aspect of the present invention, a method for treating teeth is provided. Particularly, the method includes the steps of providing a plurality of substantially identical connector members, wherein each of the substantially identical connector members has a certain first shape; fixing each of the plurality of substantially identical connector members onto a unique tooth; providing a plurality of dissimilar brackets; providing a plurality of second connector members wherein each of the plurality of second connector members is substantially identical and are adapted to be fixed to a unique one of said plurality of substantially identical connector members; causing each of said plurality of dissimilar brackets to have one of said second connector member; selecting a first of the plurality of dissimilar brackets; and attaching each of the second connector members which are located upon the selected one of the plurality of dissimilar brackets to a unique one of the plurality of substantially identical connector members.

These and other features, aspects, and advantages of the present invention will become apparent by a reading of the detailed description of the preferred embodiment of the invention, including the subjoined claims and by reference to the drawings.

DETAILED DESCRIPTION OF THE PREFERRED EMBODIMENT OF THE INVENTION

Figure 1:
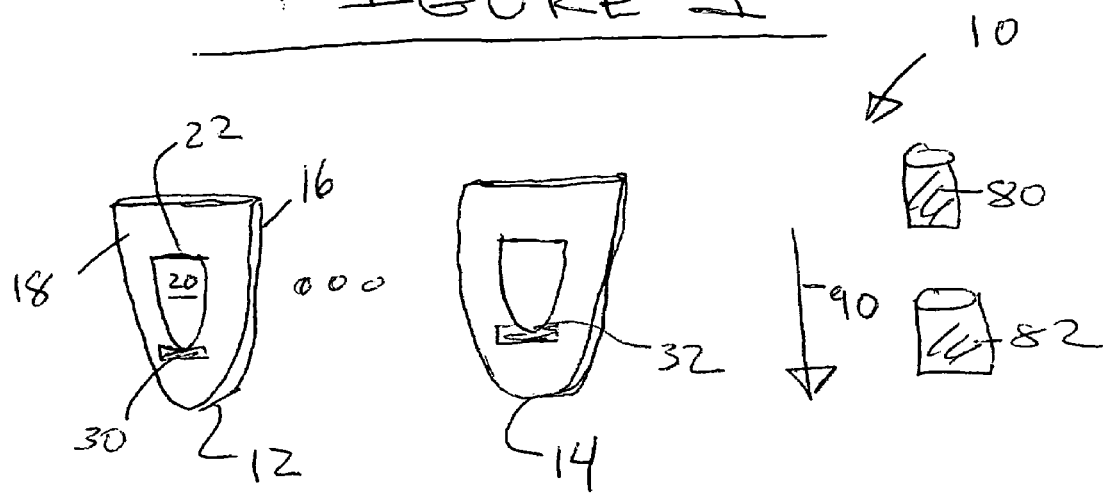
FIG. 1 is a perspective view of a orthodontic connector assembly which is made in accordance with the teachings of the preferred embodiment of the invention.

Referring now to FIG. 1, there is shown an orthodontic connector assembly 10 which is made in accordance with the teachings of the preferred embodiment of the invention.

Particularly, the orthodontic connector assembly 10 includes a plurality of substantially identical connector members, such as members 12, 14 which may be constructed from plastic or another composite material and which includes a first substantially flat back surface 16 and a second substantially flat front surface 18. The connector members, such as members 12, 14 are of a size and a shape which is smaller than the size and shape of a tooth. Nothing in this description is meant to limit the members 12, 14 to any particular size and shape.

The surface 18 includes a portion 20 which is hingedly coupled to the surface 18 along the edge 22 and thus normally contacts (i.e., is biased against) surface 18 but may be selectively moved from this first surface contacting position to a second non-contacting position away from surfaces 18 and 16. The surface 18 further includes a raised edge portion 30 upon which the far edge 32 of portion 20 overlays (e.g., the term "far edge", in this context, means the part of portion 20 farthest away form edge 22).

The connector assembly 10 further includes at least one bracket 40 having a back surface 42 upon which a pocket portion 44 is formed. The at least one bracket 40 may have a front portion 41 of any desired size and shape therapeutic configuration and the pocket portion 44 is adapted to receive the portion 20, of a member 12, after it is raised off of the surface 18 that it normally is biased against by the edge 22. After the pocket 44 receives the raised portion 20 (e.g., the portion 20 is inserted through opening 43 of the pocket portion 44) it is ensured that the bottom edge 50 of the pocket portion 44 is supported by edge 30 and then the raised portion 20 is allowed to be biased back toward surface 18 by the biasing edge 22, thereby fixing the pocket portion 44 against the surface 18 and attaching the bracket 40 to the portion 12. The edge 30 cooperates with the edge 50 to further attach the bracket 40 to the member 12. It should be appreciated that bracket, such as bracket 70, which may be dissimilar to bracket 40 is made to have a substantially identical back surface 72 which is similar to back surface 41 (i.e., each dissimilar bracket is made to have a similar back surface and thereby includes a substantially identical pocket 44). Thus, every bracket to be utilized as part of or in combination with the assembly 10 must include a back portion which is substantially similar to back portions 42, 72 (e.g., having a pocket portion 44) but may have a unique and therapeutic front portion (i.e., a portion which receives a wire). In this manner, the therapeutic front portion (e.g., portion 41) always outwardly extends from the front surface 7 of each tooth (e.g., the surface which is visible).

The connector assembly 10 may also include a quantity of cement or an adhesive 80 and some etching material or acid 82. In other non-limiting embodiments of the invention, the assembly 10 does not include the adhesive 80 or etching material 82 or any brackets, such as bracket 40.

Figure 2:
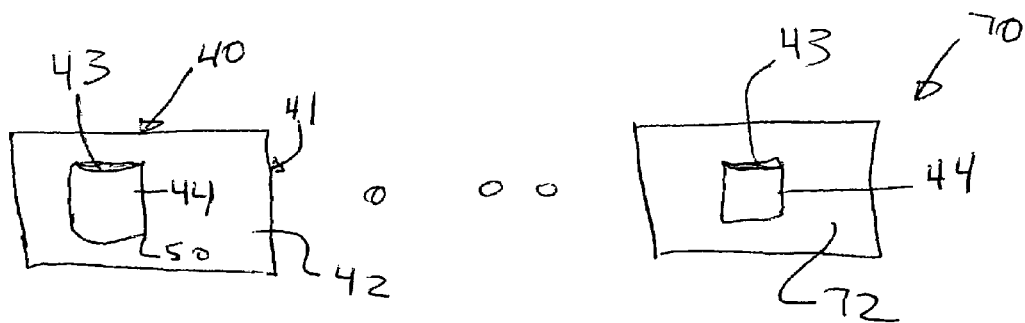
FIG. 2 is a partial front view of a portion of a patient's mouth showing a partial deployment of the orthodontic connector assembly which is shown in FIG. 1, upon certain teeth.
Figure 2:
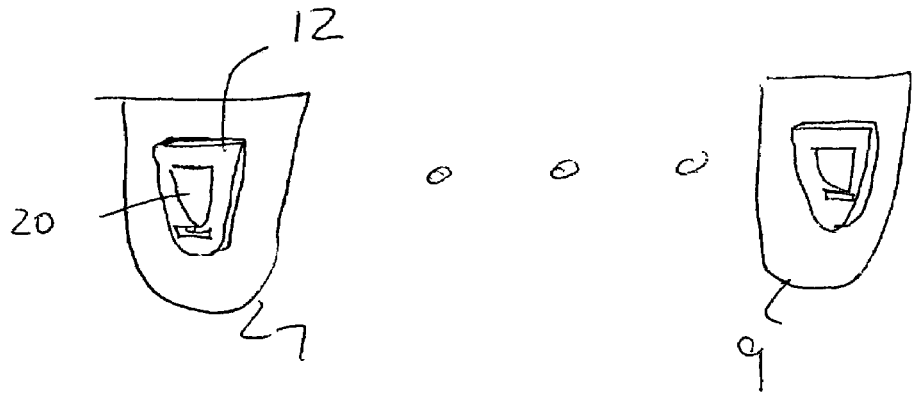
Figure 3:
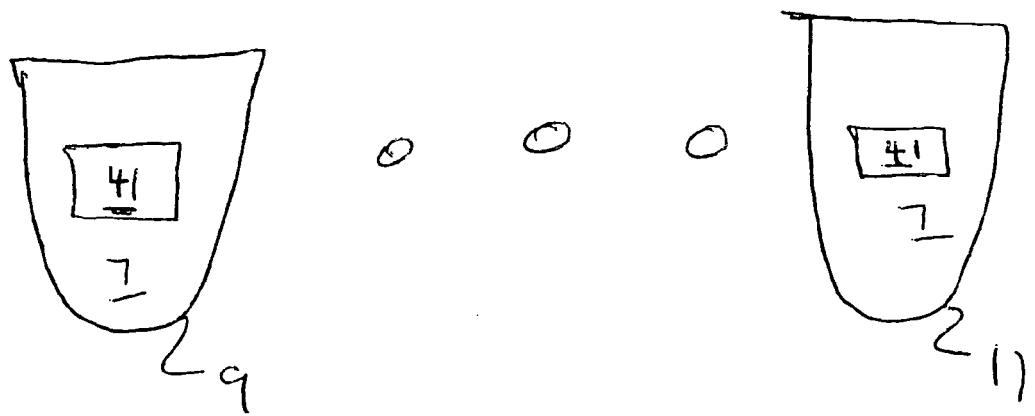
FIG. 3 is a partial front view of a patient's mouth into which the orthodontic connector assembly of the preferred embodiment of the invention is operatively deployed.

As shown best in FIGS. 2 and 3, teeth, such as teeth 9, 11, which are to receive the members 12 are first etched with the material 82 and then the material 80 is applied to the previously etched teeth and then the surface 16 of each member 12 is placed onto a respectively unique tooth, until all of teeth which are to be therapeutically manipulated have received a unique member 12.

Brackets, such as bracket 40 may be easily applied and removed from each of the deployed members 12 (e.g., a bracket, such as bracket 40 is removed simply by moving the portion 20 away from the surface 18 and sliding the pocket 44 downwards in the direction 90). In this manner, brackets, such as bracket 40, may be easily applied and removed from teeth.

It is to be understood that the various inventions are not limited to the exact construction or methodology which has been delineated above, but that various changes and modifications may be made without departing from the spirit and the scope of the inventions as are delineated in the following claims. Thus, it should be appreciated that this forgoing invention describes a system technique by which dissimilar brackets are made to have a common back portion 42, 72 which is selectively and removably receive a standardized portion 20 which has been placed upon teeth. In this manner, dissimilar brackets (e.g., those with different therapeutic or "wire receiving" frontal portions) may be easily placed upon and removed from teeth (e.g., from portion 20). It should also be appreciated that the shape of portions 20 and pocket 44 may change as desired and that nothing in this description is meant to limit these shapes in any manner.

What is claimed is:

1. An orthodontic connector assembly comprising a tapered body with a first broad edge and a second smaller edge, said tapered body having first and second opposed flat surfaces, wherein said second flat surface is selectively attached to a tooth, said orthodontic connector assembly further having a portion which is smaller than said tapered body and of substantially the same shape as said tapered body and which is movably disposed upon and coupled to said first flat surface, wherein said portion has a first broad edge which is hinged to said first flat surface and wherein said first broad edge which is hinged to said first flat surface is parallel to said first broad edge of said tapered body and wherein said portion is selectively movable from a first position in which said portion contacts said first flat surface to a second position away from said first flat surface and wherein said portion further includes a small edge, wherein said tapered body further includes a raised edge which is parallel to said first broad edge of said tapered body and which contact said small edge of said portion when said portion is in said first position; and a bracket having a back surface which includes a outwardly protruding second portion which cooperates with said back surface to form a pocket having an opening which selectively receives said portion when said portion is placed into said second position and wherein said pocket includes an edge which abuts said raised edge when said portion is placed into said first position after said portion is received by said pocket, whereby said bracket is cooperatively secured to said member after said portion is received within said pocket and moved to said first position, and wherein said bracket includes a therapeutic front surface.

2. The Orthodontic connector assembly of claim 1 where said portion is normally biased against said first flat surface.

3. The Orthodontic connector assembly of claim 2 wherein said tapered body has a "u-shaped" cross sectional area.

4. The Orthodontic connector assembly of claim 3 wherein said raised edge is substantial rectangular in shape.

* * * * *